United States Patent [19]

Siddall et al.

[11] Patent Number: 4,833,222

[45] Date of Patent: May 23, 1989

[54] CROSSLINKER STABILIZER FOR PREPARING ABSORBENT POLYMERS

[75] Inventors: Jonathan H. Siddall; Thomas C. Johnson, both of Midland, Mich.

[73] Assignee: The Dow Chemical Company, Midland, Mich.

[21] Appl. No.: 111,229

[22] Filed: Oct. 22, 1987

[51] Int. Cl.$^4$ .......................... C08F 2/00; C08F 30/04
[52] U.S. Cl. .................................. 526/200; 526/202; 526/240; 526/318.43
[58] Field of Search ...................... 526/317.1, 200, 202, 526/240, 318.43

[56] References Cited

U.S. PATENT DOCUMENTS

| | | | |
|---|---|---|---|
| 4,286,082 | 8/1981 | Tsubakimoto et al. | 524/493 |
| 4,367,323 | 1/1983 | Kinuira et al. | 526/317.1 |
| 4,677,174 | 6/1987 | Alexander et al. | 526/317.1 |
| 4,683,274 | 7/1987 | Nakamura et al. | 526/317.1 |

FOREIGN PATENT DOCUMENTS

| | | | |
|---|---|---|---|
| 8402139 | 6/1984 | European Pat. Off. | 526/317.1 |
| 61-243805 | 10/1986 | Japan | 526/317.1 |
| 62-95308 | 5/1987 | Japan | 526/317.1 |

*Primary Examiner*—Joseph L. Schofer
*Assistant Examiner*—N. Sarofim

[57] ABSTRACT

A process for the preparation of an absorbent polymeric composition is disclosed. The process involves the polymerization of an aqueous solution of carboxylic acid monomers in a neutralized or partially neutralized form in the presence of a dispersing agent which aids in the even dispersion of the crosslinking agent. The polymers prepared exhibit high absorptive capacities and low water-soluble polymer content.

19 Claims, No Drawings

CROSSLINKER STABILIZER FOR PREPARING ABSORBENT POLYMERS

This invention relates to a process for producing a crosslinked absorbent resin composition.

BACKGROUND OF THE INVENTION

Water-swellable polymers are used as constituents in sanitary materials which absorb body fluids such as: sanitary napkins, incontinent devices and disposable baby diapers. Examples of such polymers are disclosed in U.S. Pat. Nos. 3,926,891, 4,190,562 and 4,293,609, herein incorporated by reference.

The high level of water-soluble polymers is of concern in such materials because the extractable polymers may be leached from the absorbent structure by aqueous fluids which lessens the efficiency of the product. A high level of water-solubles can cause low water-absorbing capacity in the adsorbent device. Thus, when these water-swellable polymers are contacted with catamenial blood, urine, or other body fluids, they have low initial absorption rates, less effective absorption and become sticky. Therefore, a high water-soluble polymer content can inhibit the absorptive capacity of the absorbing device.

Various processes are known for producing the absorbent polymers such as: bulk polymerization, aqueous solution polymerization, spray polymerization, inverse emulsion polymerization, inverse suspension polymerization and the like.

Generally, the water-swellable, crosslinked, hydrophilic polymers are prepared by the radical copolymerization of an aqueous solution of an appropriate monomer and a crosslinking monomer. The resulting hydrous gel is dried and then pulverized to put it in the form which is useful for incorporation into devices used for the absorption of human fluids. The water-soluble, non-crosslinking monomer of the acid type may be polymerized in two forms. First, the polymerization may be performed on a carboxylic acid monomer in its acid form, and secondly the polymerization can be carried out on the carboxylic acid monomer in its neutralized form, preferably an alkali metal salt form.

When the polymerization is performed on the acid form of the monomer it is necessary to neutralize the resultant polymer in order to impart absorbent properties and make it compatible with human applications. Such neutralization has been carried out after the monomer has been polymerized into a viscous gel which is difficult to handle. The neutralization is accomplished by contacting the viscous gel with an amount of basic solution or material effective to neutralize the acid groups present in the polymer. The neutralization is impaired due to the difficulty in mixing the neutralizing agent evenly into the polymerized gel.

When using the monomers in the acid form the crosslinking monomer is soluble in the aqueous acid monomer and therefore allows for uniform mixing of the crosslinking monomer and the aqueous acid monomer. The uniform mixing aids in the formation of a polymer which is evenly and uniformly crosslinked. This may affect the amount of water-soluble polymers which are present in the absorbent polymer product. In effect, the uniform distribution of the crosslinking monomer may reduce the amount of water-soluble polymer which may leach out of the absorbent polymer when contacted with the fluid to be absorbed.

However, if the monomers are polymerized in a neutralized form, such as in a salt form, the crosslinker may not be soluble in the monomer solution and will therefore not be uniformly distributed in the monomer solution. The lack of uniform distribution may increase the concentration of water-soluble polymers present in the absorbent polymer.

U.S. Pat. No. 4,286,082, herein incorporated by reference, discloses a process for preparing an absorbent polymer composition by polymerizing an aqueous solution of a mixture of an alkali metal acrylate and acrylic acid and a crosslinking monomer in the presence of a surface-active agent. The surface-active agent acts to uniformly disperse the crosslinking monomer in the alkali metal salt and acrylic acid solution. However, the presence of a surface-active agent in the resultant polymer can inhibit the desired wicking ability of aqueous fluids through absorbent structures containing the polymer. The surface-active agent reduces the surface tension of the fluid to be absorbed resulting in an absorbent capacity of the absorbent device which is not fully utilized.

Absorbent devices often contain a wicking fibrous material which serves as an aid in the distribution of the fluid to be absorbed by the device. Examples of such wicking fibrous materials include cellulose batting, paper, woven or non-woven cloth, cellulosic fluff and the like. The wicking material distributes the fluid throughout the device so that ideally all of the absorbent polymer in the device is contacted with the fluid. This results in an efficient use of the absorbent polymer which is in the device. A capillary action between the fluid and the wicking material results in the distribution of the fluid. Such action is dependent on the surface tension of the fluid which is being distributed. Surface-active agents function to reduce the surface tension or the interfacial tension between two liquids when dissolved in water or water solutions. This reduction in surface tension can have the effect of reducing the capillary action between the fluid and the wicking material. This results in an under-utilization of the absorbent capacity of the absorbent device. Therefore the preferred dispersants are those which do not adversely affect the wicking action of the absorbent device.

An absorbent polymer composition prepared from a neutralized monomer solution which does not contain a surface-active agent which impedes capillary action in absorbent articles would be desirable. Minimizing the extractable content of the polymer composition in aqueous fluids is also desirable. Further, preparing the polymer in the absence of a surface-active agent enables one to better utilize the full absorbent capacity of the absorbent device in which the polymer is a constituent. Thus, a process for the polymerization of a neutralized monomer solution without using a surface-active agent to obtain a polymer low in extractables is desired. Such polymers should desirably exhibit good gel strengths, high rates of absorption, low levels of water-soluble polymer, and high capacities for absorbing fluids.

SUMMARY OF THE INVENTION

Accordingly, the present invention relates to a process for preparing an absorbent polymer from a neutralized monomer without a surface-active agent. The process comprises the steps of (a) preparing a dispersion of an effective amount of a crosslinking monomer and a dispersing agent in an aqueous solution of a water-soluble $\alpha,\beta$-ethylenically unsaturated carboxylic acid monomer which is at least partially neutralized, (b) subjecting the dispersion to reactive conditions so as to polymerize the neutralized or partially neutralized carboxylic acid and crosslinking monomer, wherein the dispersing agent does not reduce the surface tension of a supernatant solution of 1 grams (g) of the polymerized monomer in 200 ml of a 0.9 percent sodium chloride below about 60 dynes/cm. The surface tensions described herein are measured on a Du Nouy tensiometer using standard techniques.

The present invention also relates to a process for preparing an absorbent polymer composition comprising the steps of (1) forming an aqueous solution of a crosslinking monomer in a water-soluble $\alpha,\beta$-ethylenically unsaturated carboxylic acid monomer in the presence of an amount of a dispersing agent effective to maintain the dispersion of the crosslinking monomer after the water-soluble monomer has been neutralized, the dispersing agent being chosen such that the surface tension of a supernatant solution of 1 g of the polymerized monomer in 200 ml of a 0.9 percent sodium chloride is not less than about 60 dynes/cm, (2) neutralizing the monomer solution with an amount of basic material sufficient to neutralize a substantial portion of the monomer solution, (3) adding one or more vinyl addition polymerization initiators to the neutralized monomer solution, and then (4) subjecting the neutralized solution to polymerization conditions.

In another embodiment the present invention relates to a process for preparing an absorbent polymer composition comprising the steps of (1) dissolving a crosslinking monomer in an aqueous solution of a water-soluble $\alpha,\beta$-ethylenically unsaturated carboxylic acid monomer, (2) neutralizing the monomer solution with an amount of basic material sufficient to neutralize a substantial portion of the monomer solution, (3) contacting the neutralized solution with an amount of a dispersing agent effective to maintain the dispersion of crosslinking monomer in the neutralized monomer solution, the dispersing agent being chosen such that the surface tension of a supernatant solution of 1 g of the polymerized monomer in 200 ml of a 0.9 percent sodium chloride is not less than about 60 dynes/cm, (4) adding one or more initiators to the neutralized monomer solution, and then (5) subjecting the solution to polymerization conditions.

The present invention provides a means for preparing highly absorbent polymers from monomers which have been neutralized prior to polymerization, thus allowing for easier handling and processing of the polymer. The polymers prepared by this process exhibit excellent rates of absorption, gel strengths, low levels of water-soluble polymer which are all desirable characteristics for polymers to be employed in devices used to absorb and retain human body fluids.

DETAILED DESCRIPTION OF THE INVENTION

Types of Monomers

Suitable water-soluble $\alpha,\beta$-ethylenically unsaturated carboxylic acid monomers which are useful in the present invention include those monomers which are capable of conversion by aqueous solution polymerization into a water-swellable and/or lightly crosslinked hydrophilic gel polymer. The crosslinked structure may be obtained by the copolymerization of a water-soluble monomer and a crosslinking monomer possessing at least two polymerizable double bonds in the molecular unit. Examples of such monomers include $\alpha,\beta$-ethylenically unsaturated monomers such as mono and polycarboxylic acids.

The water-swellable or lightly crosslinked hydrophilic polymers that are prepared by the method of the present invention can be any of the known hydrophilic polymers which are capable of absorbing large quantities of fluids. Examples of such polymers are disclosed in U.S. Pat. Nos. 3,997,484, 3,926,891, 3,935,099, 4,090,013, and 4,190,562 herein incorporated by reference. Such hydrophilic polymers are prepared from water-soluble $\alpha,\beta$-ethylenically unsaturated monomers such as mono and polycarboxylic acids and acrylamide and its derivatives.

Examples of suitable monocarboxylic acids include acrylic acid, methacrylic acid, crotonic acid, and isocrotonic acid, alkali metal salts and ammonium salts thereof. Suitable polycarboxylic acids include maleic acid, fumaric acid, and itaconic acid. Suitable acrylamide derivatives include methacrylamide. The preferred monomers include acrylic acid and methacrylic acid and their respective salt forms such as alkali metal or ammonium salts.

The concentration of monomer which is used is largely dependent on the ultimate properties which are desired in the final polymer product. Such properties include good gel strength, high absorbent capacity, fast rates of absorption and low levels of water-soluble polymer. It is desirable to use a concentration of monomer which results in an efficient level of conversion of monomer to polymer, preferably at least about 80 percent, more preferably at least about 90 percent and most preferably at least about 99 percent conversion. The water-soluble monomers useful in the present invention may be used in amounts ranging from about 10 percent to about 80 percent weight based on the total weight of the aqueous monomer solution. Preferably, the amount ranges from about 20 percent to about 60 percent based on the total weight of the aqueous monomer solution.

Optionally, minor amounts of other water-soluble, unsaturated monomers may be present such as alkyl esters of the acid monomers. For example, methyl acrylate or methyl methacrylate may be present.

The polymerization is carried out on carboxylic acid monomers which have been neutralized prior to the polymerization. This neutralization is conveniently achieved by contacting the aqueous monomer with an amount of basic material sufficient to neutralize at least about 20 percent, preferably at least about 50 percent of the acid groups present in the acid monomers. The range is typically, from about 20 to about 95 percent, preferably from about 50 percent to about 85 percent, and most preferably about 65 percent to about 80 percent of the acid groups present in the acid monomers. When pre-neutralizing the monomer solution it is important to control the neutralization conditions so that the heat of neutralization does not cause the premature polymerization of the monomer mixture. The neutralization is advantageously carried out at temperatures below about 40° C., preferably below about 35° C. The neutralization of the monomers causes the crosslinking monomer to become insoluble in the monomer solution as is evidenced by the formation of a cloudy solution. The insolubility of the crosslinking monomer can result in a polymer which is not uniformly crosslinked and therefore tends to have a high level of water-soluble polymer content.

The use of the pre-neutralized monomer allows for the production of an absorbent polymer which does not need to be neutralized either after polymerization or prior to incorporation into absorbent devices. The polymer prepared from the pre-neutralized monomer is already in the alkali metal salt form. The pre-neutralized polymers exhibit absorbent properties which are highly desirable for polymers which are to be used as constituents in human fluid absorbent devices.

Conveniently, a conventional vinyl addition polymerization initiator is used in the polymerization of the water-soluble monomers and the crosslinker. A free radical polymerization initiator which is sufficiently soluble in the monomer solution to initiate polymerization is preferred. For example, water-soluble peroxides such as potassium persulfate, ammonium persulfate, sodium persulfate, and other alkali-metal persulfates, hydrogen peroxide and water soluble azo-compounds such as 2,2'-azobis(2-amidinopropane·HCL). Some of these initiators, such as hydrogen peroxide can be combined with reducing substances such as sulfites or amines to form known redox type initiators. The amount of initiator used may range from about 0.01 to about 1.0 weight percent, preferably 0.01 to about 0.5 weight percent, based on the total weight of monomer reactants. Alternatively, the free radicals can be generated in situ by ultraviolet excitation or X-rays. A preferred method of the invention involves the use of hydrogen peroxide with the initiator or as part of the initiators. The hydrogen peroxide imparts what is thought to be a bleaching effect on the resultant polymer. A polymer having color is generally less desirable for aesthetic reasons.

When thermal initiators are used the selection of reaction temperature typically depends on the type of initiator used and the type of monomer chosen. The polymerization temperature for the polymerization is preferably a relatively low temperature which increases the molecular weight of the resulting crosslinked polymer. Generally, the reaction temperature may range from about 5° C. to about 100° C.

Types of Crosslinking Monomers

Organic compounds having two or more ethylenic groups copolymerizable with the water-soluble monomers can be used as the crosslinking monomers. Exemplary crosslinking monomers include diacrylate or dimethacrylate of ethylene glycol, diethylene glycol, triethylene glycol, propylene glycol, 1,4-butane diol, 1,5-pentane diol, 1,6-hexane diol, neopentyl glycol, trimethylol propane and pentaerythritol, triacrylates or trimethacrylates of trimethylol propane and pentaerythritol, tetracrylates or tetramethacrylates of pentaerythritol, N,N'-methylene-bis-acrylamide, N,N'-methylene-bis-methacrylamide and triallyl isocyanurate, and the like. The preferred crosslinking monomers for the present invention are those crosslinking monomers which are not soluble in the neutralized monomer solution such as trimethylolpropanetriacrylate. The lack of solubility of the crosslinking agent results in the necessity for the dispersing agent.

The crosslinking monomer is present in the dispersion of water-soluble monomer and dispersing agent in an amount effective to crosslink the water-soluble polymer. Typically the crosslinking monomer is used in amounts ranging from about 0.0001 to about 5 parts by weight based on 100 parts by weight of water-soluble monomer used. More preferably, the amount ranges from about 0.01 to about 2 parts by weight, and most preferably, from about 0.02 to about 1 part by weight, per 100 parts by weight of the water-soluble monomer. If an amount over 5 parts by weight of crosslinking monomer is used the resulting polymer has too high a crosslinking density and exhibits a reduced absorption capacity, if the crosslinker is used in an amount less than about 0.0001 part by weight the polymer has too low a crosslinking density and when contacted with the fluid to be absorbed becomes sticky and exhibits a lower initial absorption rate. The preferred amount of crosslinking monomer is determined by the desired degree of absorption capacity and the desired strength to retain the absorbed fluid.

Solubility in Neutralized Acid Solutions

Generally, such crosslinking monomers are to a large extent soluble in an aqueous solution of the monomers in acid form as indicated by the clarity of these solutions. However, when the monomer in acid form is neutralized some of the crosslinking monomers tend to exhibit a reduced solubility. This is typically evidenced by the formation of a cloudy solution after the neutralization of the acid monomer solution indicating a phase separation between the crosslinking monomer and the water-soluble monomer.

It is believed that the insolubility of the crosslinking monomers in the neutralized water-soluble monomer causes the crosslinker to be unevenly distributed throughout the polymer product. This appears to have the effect of increasing the level of water-soluble polymers which are present and capable of leaching out of the polymer. Therefore, it is desirable to uniformly disperse the crosslinking monomer in order to produce a water absorbent polymer from a neutralized monomer, in which the polymer is uniformly crosslinked, exhibits low levels of water-soluble polymer, and good absorptive properties.

Suitable dispersing agents are identified in part by the surface tension of a solution in a standard test as follows. One gram of polymer which has been prepared in the presence of the dispersing agent, is mixed in 200 ml of a 0.9 percent solution of sodium chloride and the surface tension of the supernatant of that solution is tested using a Fisher brand Du Nouy tensiometer. Those dispersing agents which will maintain a surface tension of the supernatant of at least about 60 dynes/cm are suitable. Preferably, the supernatant will not have a surface tension less than about 65 dynes/cm and most preferably, not less than about 70 dynes/cm.

Suitable dispersing agents have the ability to maintain a uniform dispersion of crosslinking monomer in the neutralized water-soluble monomer solution. Such dispersing agents do not necessarily render the crosslinker soluble in the neutralized monomer solution but rather function as an aid n the maintenance of a fine dispersion of the crosslinking monomer in the water-soluble monomer. A good dispersion of crosslinker in the water-soluble monomer is evidenced by a cloudy solution of water-soluble monomer that does not separate prior to or during polymerization. Examples of suitable dispersing agents include carboxymethylcellulose suspending aids, methyl cellulose, hydroxypropyl cellulose, with polyvinyl alcohol being preferred and about 75 to about 100 percent hydrolyzed polyvinyl alcohol being most preferred.

The dispersing agent must be chosen such that when the recovered and dried water-absorbent polymer is incorporated into a human fluid absorbent device the dispersing agent residue does not enter human fluids to which it is exposed and inhibit the wicking action of the absorbent device. This is important since it is the wicking action which allows the fluid to become evenly distributed within the adsorbent device which enables the absorbent polymer to be used in an efficient manner. Therefore, the dispersing agents of the present invention are those which will maintain a surface tension of the supernatant (as described above) of at least about 65 dynes/om and most preferably, at least about 70 dynes/cm. The supernatant solution is meant for the purpose of the test to simulate human fluids which have been contacted with the polymer in a human fluid absorbent device.

The dispersing agent is present in the aqueous solution of the crosslinking monomer and water-soluble monomer in an amount effective to maintain the dispersion of the solution prior to and during the polymerization. Typically the amount of dispersing agent present in the aqueous solution is from about 1 to about 0.001 weight percent based on the weight of water-soluble monomer present. Preferably, the amount of dispersing agent present in the aqueous solution is from about 0.1 to about 0.005 weight percent, more preferably from about 0.01 to about 0.05 weight percent based on the weight of water-soluble monomer present.

Methods and Materials Used for the Neutralization

Compounds which are useful to neutralize the carboxylic acid groups of the monomer are typically those which will sufficiently neutralize the acid groups without having a detrimental effect on the polymerization process. Such compounds include alkali metal hydroxides, alkali metal carbonates and bicarbonates. Preferably, the material used to neutralize the monomer is sodium or potassium hydroxide or sodium carbonate or potassium carbonate. The neutralizing agent is used in an amount which will sufficiently neutralize from about 20 percent to about 95 percent, preferably from about 50 percent to about 85 percent, and most preferably from about 65 percent to about 80 percent of the acid groups present in the water-soluble monomer. In determining the desired degree of neutralization care must be taken to insure that the pH of the resulting crosslinked absorbent polymer being contacted with or dispersed in an aqueous fluid to be absorbed is maintained in a range appropriate for the applications for which the polymer is intended.

A Typical Polymerization Conditions

For the aqueous-solution copolymerization according to the present invention, the water-soluble monomer, the crosslinking monomer, the dispersing agent, and the initiator are mixed in a conventional manner prior to the copolymerization. The order of mixing is not critical as long as a uniform dispersion without coalescence of the crosslinking monomer is maintained. Mixing may be effected with static in-line mixers, or any other suitable mixing apparatus. The temperature of mixing should be maintained so that the polymerization is not initiated prematurely, preferably below a temperature of about 40° C., more preferably below about 35° C. The solution may then be neutralized under the conditions described above.

In a preferred embodiment for the invention, an aqueous solution of the monomer in the acid form, the crosslinker and the dispersing agent is prepared. The aqueous solution is then neutralized resulting in a dispersion of the crosslinker in a solution of the neutralized acid monomer.

The polymerization of the mixture may be initiated by elevating the temperature of the mixture containing the initiator or by using a redox-type initiator as described above. Generally, the temperature at which polymerization will begin ranges from about 20° C. to about 45° C. The temperature at which the polymerization is carried out is highly dependent on the type of monomers used and the specific initiator system employed. Preferably, the maximum temperature of polymerization ranges from about 50° C. to about 100° C., most preferably from about 60° C. to about 90° C. The method by which the temperature of the polymerization is controlled is not critical so long as sufficient cooling is present to remove the heat which is generated during the polymerization. In a preferred embodiment of this invention, water-solubles level in the polymer from a monomer neutralized process can be controlled by careful control of the temperature during the exothermic polymerization. External cooling jackets alone are generally not adequate to provide the desired reaction temperature control when a large reaction vessel is used. Conducting the reaction under reduced pressure is desirable to control temperature.

The resulting hydrous gel-like polymer may be used to prepare the absorbent polymer composition by drying of the hydrous polymer. It is desirable to dry the gel-like hydrous polymer at as high an efficiency and in as short a time as possible in order to prevent the deterioration of the polymer due to excessive heat. A desirable method of drying comprises heating the polymer by hot air to a temperature of about 50° C. to about 200° C., for a period of time sufficient to reduce the moisture content of the hydrous polymer to below about 40 percent, preferably below about 10 percent based on the total weight of absorbent polymer.

The absorbent polymer composition obtained by drying the gel-like hydrous polymer under heat is suitably comminuted into coarse particles, granules or a powder depending upon the desired size. The method of pulverization is not generally critical, and any method known in the art can be suitably employed. Agitation of the reaction medium during polymerization can also be used to control particle size.

The absorbent polymer composition of the present invention has excellent performance characteristics. The polymer has a high degree of polymerization because it has been prepared from the gel-like hydrous polymer formed by copolymerization in an aqueous solution in a relatively high concentration. Moreover, it is efficiently and uniformly crosslinked by copolymerizing the water-soluble monomer and the crosslinking monomer in the presence of the dispersing agent. Therefore, the absorbent polymer composition has a very low water-soluble polymer content, and thus, is less sticky when in contact with an aqueous fluid and has a large amount of saturated absorption. The polymer composition exhibits a water-soluble polymer content of less than bout 20 percent, preferably less than about 15 percent, and most preferably less than about 10 percent based on the total weight of the absorbent polymer. Water soluble polymer content is determined by extracting 1 g of absorbent polymer for 4 hours with 500 g of 0.9 percent sodium chloride. The swollen polymer is filtered off and the filtrate titrated with hydrochloric acid to determine the level of soluble polymer present.

The absorbent polymer compositions of the present invention exhibit absorbent capacities ranging from about 20 g/g to about 70 g/g, more preferably from about 30 g/g to about 55 g/g, and most preferably from about 40 g/g to about 50 g/g. The absorbent capacity or free swell capacity (FSC) is determined by allowing 1.0 g of the polymer to absorb its limit of 300 g of a 0.9 percent sodium chloride solution in 20 minutes. The excess salt solution which is not absorbed is weighed and subtracted from the original 300 g to give the free swell capacity value.

EXAMPLES

The following examples illustrate preparation of preneutralized polymer and physical properties of the polymer, i.e., performance data.

Example 1

In a 1-liter glass reactor is dissolved 0.31 g (0.25 percent based on the weight of monomers) of trimethylolpropanetriacrylate (TMPTA) in 125 g of acrylic acid. To this solution 323.2 g of distilled water is added. To this solution is added 3 ml of a solution of 1 g of Vinol® 523 ™, a polyvinyl alcohol available from Air Products and Chemical Inc., dissolved in 278 g of distilled water. With agitation 97 g of 50 percent sodium hydroxide is then slowly added to the solution in order to neutralize the acid groups of the monomer. The reactor is cooled to maintain a temperature of about 30° C. The neutralization causes the TMPTA to "fall out" of the solution as an ultrafine, very stable, dispersion. With the agitation continued, 6 drops of Versenex ™-80 (40 percent aqueous solution of pentasodium salt of diethylene triaminepentaacetic acid), available from The Dow Chemical Company, is added to the solution with 0.031 g of V-50 (2,2'-azobis(2-amidinopropane·HCL)) available from Wako Chemicals USA, and 0.031 g of sodium persulfate. The solution is deoxygenated with $N_2$. This solution is then added over a period of 12 minutes to a 2 liter glass reactor which has been preheated to a temperature of 90° C. The reactor is maintained at a temperature of no more than 85° C. by a heated jacket around the reactor. The reaction is allowed to run until complete as evidenced by a reduction in heat generation. The reaction contents are held at a reaction temperature 85° C. after completion of reaction. The polymer gel is then removed from the reactor, ground and dried in an oven at 100° C.

The absorbent properties are determined by the following procedures:

1. Free swell capacity (FSC) is determined by allowing 1.0 g of the polymer to absorb its limit of 300 g of 0.9 percent sodium chloride solution in 20 minutes. The excess salt solution which is not absorbed is weighed and subtracted from the original 300 g to give the free swell capacity value.

2. Water soluble polymer content is determined by extracting 1 g of absorbent polymer for 4 hours with 500 g of 0.9 percent sodium chloride. The swollen polymer is filtered off and the filtrate titrated with hydrochloric acid to determine the level of soluble polymer present.

The polymer composition of this example exhibits a FSC of 44.4 g/g and a water soluble polymer content of 5.3 percent.

Example 2

In a 50 gallon glass-lined reactor 0.65 pounds of TMPTA is dissolved in 47 pounds of acrylic acid. 115.5 Pounds of deionized water is added to the reactor followed by 0.24 pounds of a 2 percent aqueous solution of PVA, Vinol 523 available from Air Products and Chemicals, Inc., and 11 g of Versenex 80, available from The Dow Chemical Company. To this solution in the reactor, 36.6 pounds of 50 percent sodium hydroxide is added slowly with good agitation while maintaining the temperature of the contents below about 30° C. by means of the reactor jacket.

This monomer mix is transferred to a 30 gallon stainless steel reactor equipped with high torque agitation. Oxygen is removed by sparging the reactor contents for 30 minutes with $N_2$. 4.3 Grams of sodium thiosulfate, 2.7 g Wako V-50, and 32.0 g sodium persulfate are added to the reactor. Within a few minutes the reactor temperature gradually begins to rise from 27° C. By maintaining the reactor at about 270 torr pressure by means of a vacuum pump and condenser, the peak temperature of the reaction is limited to 77° C. After holding the reactor contents at the peak temperature for 30 minutes, the finely divided gel is removed from the reactor and dried at 100° C.

The polymer resulting from Example 2 exhibits 6.3 percent water-soluble polymer and a FSC of 46.1 g/g.

Example 3

Using the same equipment as in Example 2, 0.70 pounds TMPTA is dissolved in 50 pounds of acrylic acid. 110.2 Pounds deionized water is added along with 11 g Versenex 80 and 0.25 pounds of a 5 percent aqueous solution of PVA (Vinol 205, available from Air Products and Chemicals, Inc.). To this solution in the reactor 38.9 pounds of 50 percent sodium hydroxide is slowly added with good agitation while maintaining the monomer mix below about 30° C. by means of the reactor jacket.

The monomer mix is transferred to a 30 gallon stainless steel reactor equipped with a high torque agitator. Dissolved oxygen is removed from the monomer mix by in-line sparging of $N_2$ during the transfer. To the reactor is added 3.4 g sodium thiosulfate, 3.4 g WAKO V-50, 45.4 g sodium persulfate, 75.6 g 30 percent hydrogen peroxide and 11.4 g Lupersol 256, (2,5-dimethyl-2,5-bis(2-ethyl hexanoylperoxy)hexane) available from Lucidol Division of Pennwalt.

Within a few minutes, the reaction mixture begins to gradually rise from 27° C. and to thicken. By maintaining the reactor at a reduced pressure the peak temperature of the reaction is limited to about 81° C. After holding the reactor contents at the peak temperature for 30 minutes, the finely divided gel is removed from the reactor and a small portion is dried at 150° C. using a hot air gun.

The polymer resulting from Example 3 exhibits 8.2 percent water-soluble polymer and a free swell capacity of 43.4 g/g.

What is claimed is:

1. A process for preparing an absorbent polymer composition comprising the steps of:
   (a) preparing a dispersion of an effective amount of a crosslinking monomer and from about 0.1 to about 0.005 weight percent of a dispersing agent in an aqueous solution of a water-soluble α,β-ethylenically unsaturated carboxylic acid monomer which is at least partially neutralized, (b) subjecting the dispersion to reactive conditions so as to polymerize the neutralized or partially neutralized carboxylic acid and crosslinking monomer, wherein the dispersing agent does not reduce the surface tension of a supernatant solution of 1 g of the polymerized monomer is 200 ml of a 0.9 percent aqueous sodium chloride below about 60 dynes/cm.

2. The process of claim 1 wherein the crosslinking monomer is selected from the group consisting of trimethylopropanetriacrylate and diethylene glycol diacrylate.

3. The process of claim 1 wherein the crosslinking monomer present in the dispersion is polymerized in an amount ranging from about 0.0001 to about 5 parts by weight based on 100 parts by weight of water-soluble monomer.

4. The process of claim 1 wherein the dispersion further comprises water soluble alkyl esters of unsaturated carboxylic acids.

5. The process of claim 1 wherein the water-soluble ethylenically unsaturated monomer is selected from the group consisting of acrylic acid, methacrylic acid, and alkali metal salts of these acids.

6. The process of claim 5 wherein the water-soluble ethylenically unsaturated monomer is present in an amount ranging from about 10 percent to about 80 percent based on the total weight of the aqueous monomer dispersion.

7. The process of claim 1 wherein the dispersing agent is selected from the group consisting of carboxymethylcellulose suspending aids, and polyvinyl alcohol.

8. The process of claim 7 wherein the dispersing agent is polyvinyl alcohol.

9. The process of claim 8 wherein the dispersion additionally comprises an effective amount of one or more vinyl addition polymerization initiators.

10. The process of claim 9 wherein initiators are selected from the group consisting of: sodium persulfate, ammonium persulfate, potassium persulfate, hydrogen peroxide, azo-bis compounds and redox-type initiators.

11. The process of claim 10 wherein the initiator is present in the dispersion in an amount of from about 0.01 to about 1.0 weight percent based on the total weight of monomer reactants.

12. The process of claim 1 wherein the dispersion is prepared by contacting an aqueous solution of crosslinking monomer, ethylenically unsaturated monomer, and the dispersing agent with a basic material effective to neutralize the acid groups of the water-soluble ethylenically unsaturated monomer.

13. The process of claim 12 wherein the basic material used to neutralize the monomer mixture is selected from the group consisting of sodium hydroxide, potassium hydroxide or sodium carbonate.

14. The process of claim 12 wherein the basic material is used in an amount effective to neutralize at least about 20 percent of the acid groups of the water-soluble ethylenically unsaturated monomer.

15. The process of claim 12 wherein the basic material is used in an amount effective to neutralize at least about 50 percent of the acid groups of the water-soluble ethylenically unsaturated monomer.

16. A process for preparing an absorbent polymer composition comprising the steps of (1) forming an aqueous solution of a crosslinking monomer in a water-soluble ethylenically unsaturated monomer in the presence of an amount of a dispersing agent effective to maintain the dispersion of the crosslinking monomer after the water-soluble monomer has been neutralized, the dispersing agent being chosen such that the surface tension of a supernatant solution of 1 g of the polymerized monomer in 200 ml of a 0.9 percent sodium chloride is not less than about 60 dynes/cm as measured on a Du Nouy tensiometer, (2) neutralizing the monomer solution with an amount of basic material sufficient to neutralize a substantial portion of the monomer solution, (3) adding one or more vinyl addition polymerization initiators to the neutralized monomer solution, and then (4) subjecting the neutralized solution to polymerization conditions.

17. The process of claim 16 wherein the polymerization conditions comprise a temperature ranging from about 5° C. to about 90° C.

18. A process for preparing an absorbent polymer composition comprising the steps of (1) dissolving a crosslinking monomer in an aqueous solution of water-soluble α,β-ethylenically unsaturated monomer, (2) neutralizing the monomer solution with an amount of basic material sufficient to neutralize a substantial portion of the monomer solution, (3) introducing into the neutralized solution with an amount of a dispersing agent effective to maintain the dispersion of crosslinking monomer in the neutralized monomer solution, the dispersing agent being chosen such that the surface tension of a supernatant solution of 1 g of the polymerized monomer in 200 ml of a 0.9 percent sodium chloride is not less than about 60 dynes/cm, (4) adding one or more vinyl addition polymerization initiators to the neutralized monomer solution, and then (5) subjecting the solution to polymerization conditions.

19. A process for preparing an absorbent polymer composition comprising the steps of:

(a) preparing a dispersion of an effective amount of a crosslinking monomer and from about 0.1 to about 0.005 weight percent of a dispersing agent in an aqueous solution of a water-soluble α,β-ethylenically unsaturated carboxylic acid monomer which is at least partially neutralized, (b) subjecting the dispersion to reactive conditions so as to polymerize the neutralized or partially neutralized carboxylic acid and crosslinking monomer, wherein the dispersing agent does not reduce the surface tension of a supernatant solution of 1 g of the polymerized monomer in 200 ml or a 0.9 percent aqueous sodium chloride below about 65 dynes/cm.

* * * * *